United States Patent [19]
Thomas

[11] Patent Number: 6,030,086
[45] Date of Patent: Feb. 29, 2000

[54] FLASH TUBE REFLECTOR WITH ARC GUIDE

[75] Inventor: Bradley Scott Thomas, Timonium, Md.

[73] Assignee: Becton, Dickinson and Company, Franklin Lakes, N.J.

[21] Appl. No.: 09/032,935

[22] Filed: Mar. 2, 1998

[51] Int. Cl.[7] .................................................. G03B 15/02
[52] U.S. Cl. ............................................ 362/16; 316/347
[58] Field of Search ............................ 362/16, 327, 347, 362/304, 348, 346, 297, 217

[56] References Cited

U.S. PATENT DOCUMENTS

| | | | |
|---|---|---|---|
| 3,199,775 | 8/1965 | Drucker | 494/19 |
| 3,741,011 | 6/1973 | Seybold | 73/149 |
| 3,955,890 | 5/1976 | Bessis et al. | 356/39 |
| 4,027,660 | 6/1977 | Wardlaw et al. | 600/589 |
| 4,077,396 | 3/1978 | Wardlaw et al. | 600/309 |
| 4,082,085 | 4/1978 | Wardlaw et al. | 600/309 |
| 4,156,570 | 5/1979 | Wardlaw | 356/36 |
| 4,194,835 | 3/1980 | Shiode . | |
| 4,428,669 | 1/1984 | Bessis | 356/39 |
| 4,434,385 | 2/1984 | Touho et al. | 313/161 |
| 4,479,720 | 10/1984 | Mochida et al. | 366/214 |
| 4,555,183 | 11/1985 | Thomas | 366/208 |
| 4,558,947 | 12/1985 | Wardlaw | 356/39 |
| 4,567,754 | 2/1986 | Wardlaw et al. | 73/61.43 |
| 4,774,965 | 10/1988 | Rodriguez et al. | 600/584 |
| 4,823,624 | 4/1989 | Rodriguez et al. | 73/865.9 |
| 4,848,917 | 7/1989 | Benin et al. | 366/110 |
| 5,195,825 | 3/1993 | Ringrose | 366/213 |
| 5,380,087 | 1/1995 | Haber et al. | 366/130 |

FOREIGN PATENT DOCUMENTS

| | | |
|---|---|---|
| 0 324 651 | 7/1986 | European Pat. Off. . |
| WO 093026034 | 12/1993 | WIPO ................................... 362/297 |

OTHER PUBLICATIONS

Stephen C. Wardlaw, MD, et al., "Quantitative Buffy Coat Analysis—A New Laboratory Tool Functioning as a Screening Complete Blood Cell Count", *Journal of the American Medical Association,* vol. 249, Feb. 4, 1983, pp. 617–620.

Robert L. Sallitt, et al., "Evaluation of Leukocyte Differential Counts on the QBC® Centrifugal Hematology Analyzer According to NCCLS Standard H20–T", *Blood Cells,* vol. 11, 1986, pp. 281–294.

QBC® Centrifugal Hematology Control Kit Brochure, Becton Dickinson and Company, 1988.

(List continued on next page.)

*Primary Examiner*—Laura K. Tso
*Assistant Examiner*—Hargobind Sawhney
*Attorney, Agent, or Firm*—Bruce S. Weintraub

[57] ABSTRACT

A combined reflector and arc guide for use with a xenon flash tube comprises a reflector structure having a reflecting surface that is adapted to be placed in a predetermined orientation with respect to the flash tube. An electrically conductive arc guide is carried by, and is preferably integral with, the reflector structure for controlling the arc in the flash tube. The arc guide comprises an elongated ridge that projects outwardly from the reflecting surface of the reflector structure, and extends in a direction substantially parallel to the longitudinal axis of the flash tube. An electrical terminal is carried by the reflector structure and has an electrical connection to the arc guide for allowing an electrical potential to be applied to the arc guide. The reflector structure is preferably made of an electrically conductive plastic material, thereby providing continuity between the electrical terminal and the arc guide without the need for a separate conductor. An area of modified reflectivity, preferably in the form of a plurality of grooves, may be provided in the reflective surface of the reflector structure to spread out the intensity peak of the flash tube. The disclosed reflector is simple and inexpensive to manufacture, and is suited for use in automated hematology systems in which a pulse of light from the flash tube causes dyed blood cell layers in a capillary tube to fluoresce so that a complete blood count can be obtained by optical imaging techniques while the blood sample is being rotated in a centrifuge.

22 Claims, 5 Drawing Sheets

OTHER PUBLICATIONS

QBC® Autoread™ Centrifugal Hematology System Brochure, Becton Dickinson and Company, 1991.

QBC® Centrifuge System Centrifuge Model 424740 Brochure, Becton Dickinson and Company, Aug., 1993.

QBC® Centrifugal Hematology Control Brochure, Becton Dickinson and Company, 1995.

QBC® Hematology Control Assay, Becton Dickinson and Company, 1996.

QBC® Autoread™ Plus Brochure, Becton Dickinson and Company, 1996.

QBC® Hematology Control Instructions for Use, Becton Dickinson and Company, published prior to 1998.

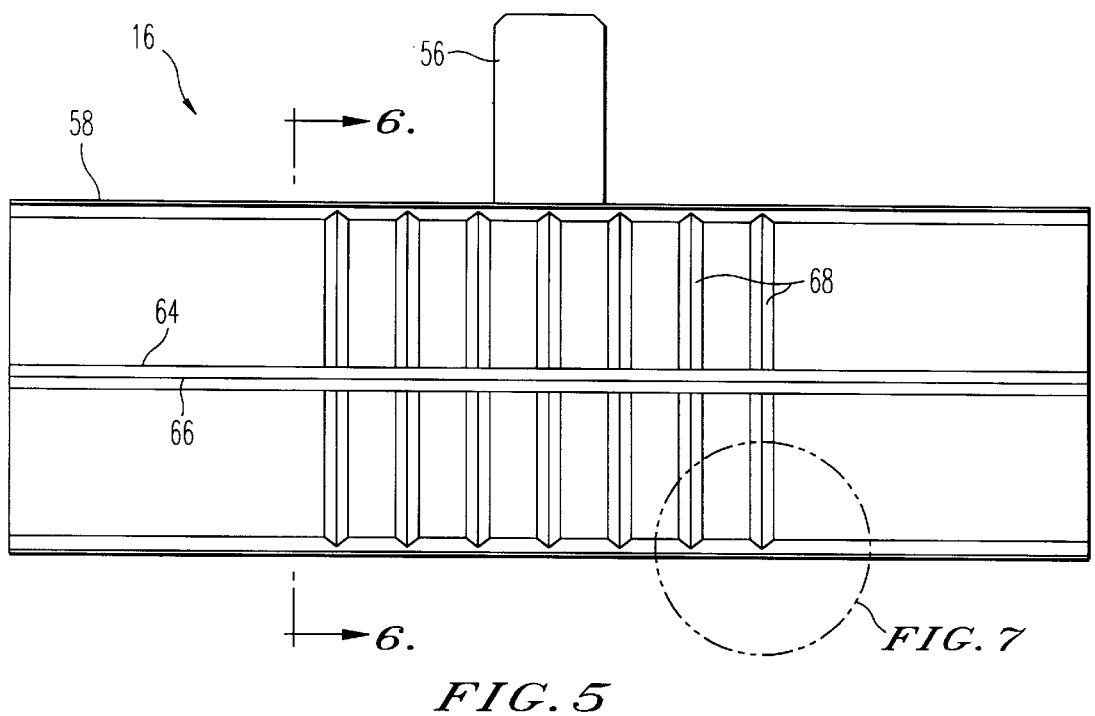
FIG. 5
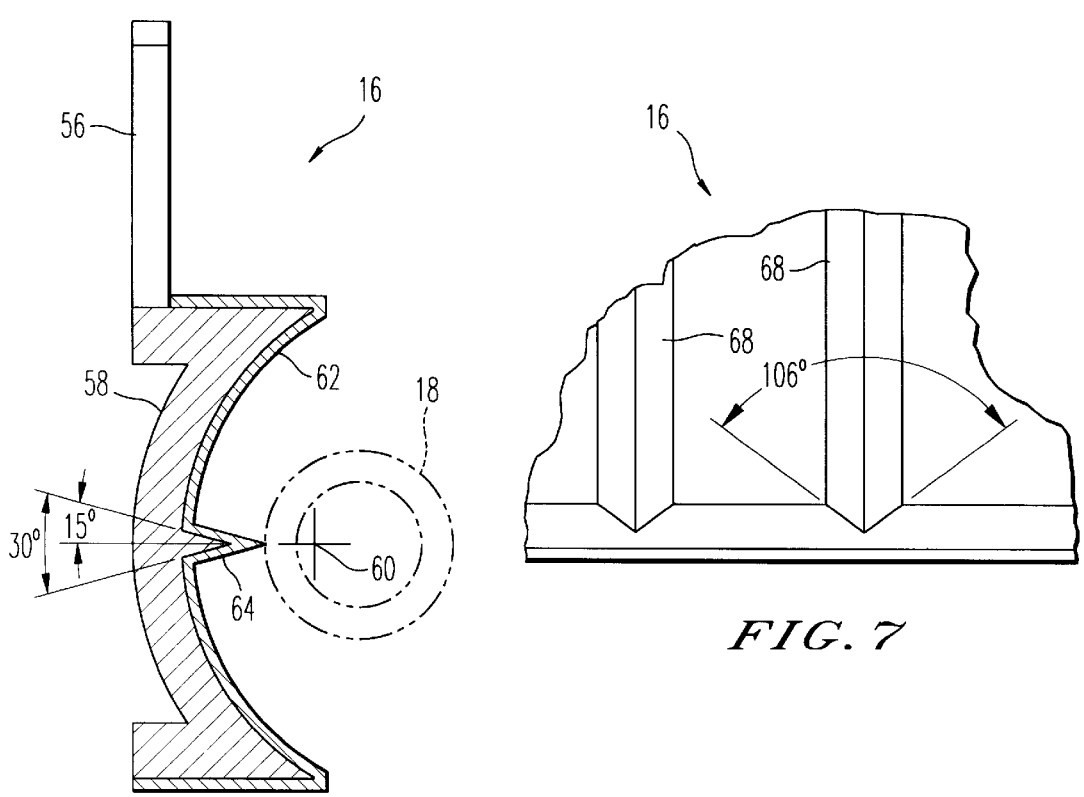
FIG. 6
FIG. 7

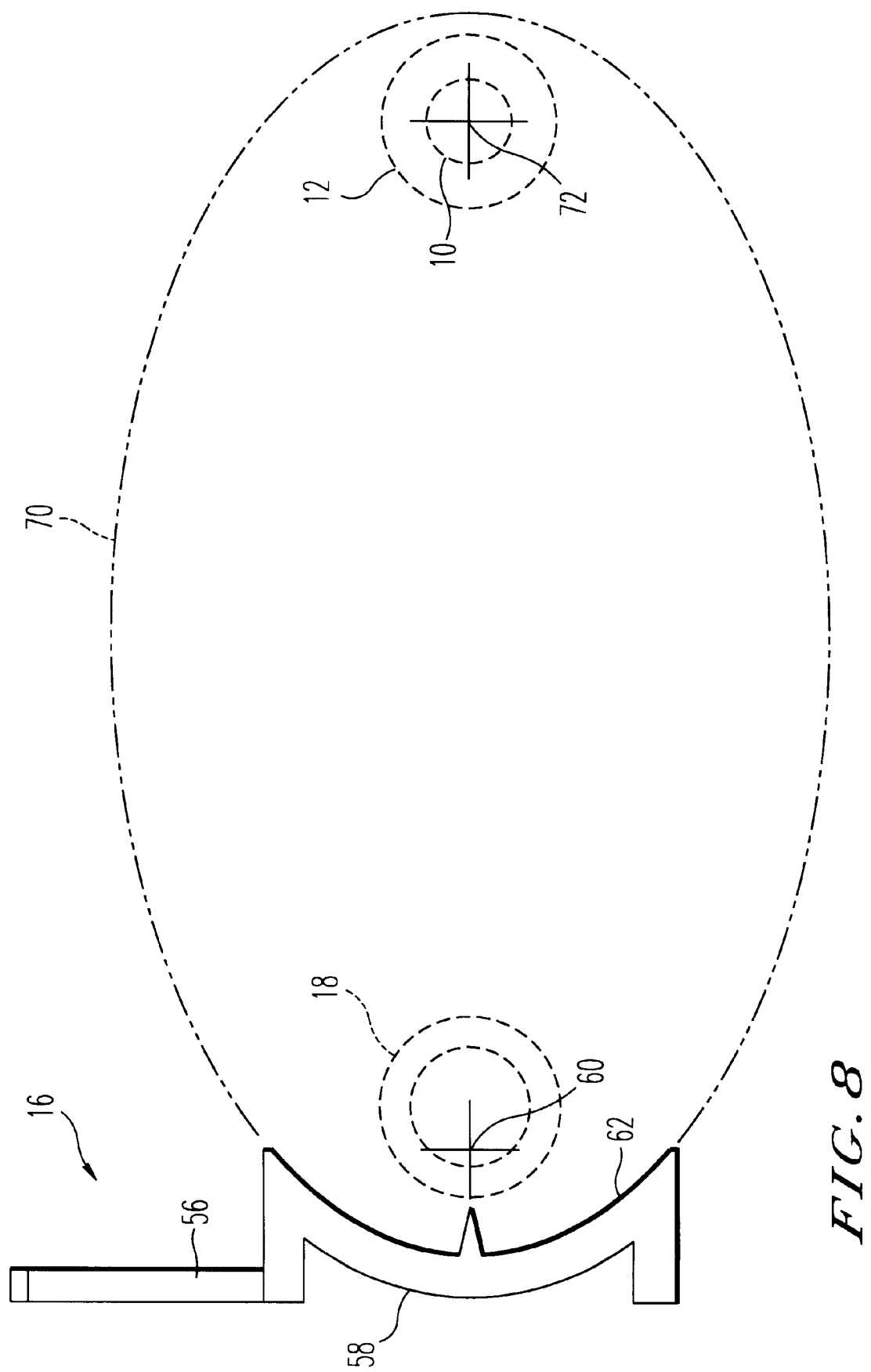

FLASH TUBE REFLECTOR WITH ARC GUIDE

CROSS REFERENCE TO RELATED APPLICATIONS

Related subject matter is disclosed and claimed in a copending U.S. patent application of Stephen C. Wardlaw entitled "Assembly for Rapid Measurement of Cell Layers", Ser. No. 08/814,536, filed on Mar. 10, 1997; in a copending U.S. patent application of Stephen C. Wardlaw entitled "Method for Rapid Measurement of Cell Layers", Ser. No. 08/814,535, filed on Mar. 10, 1997; in a copending U.S. patent application of Michael R. Walters entitled "Centrifugally Actuated Tube Rotator Mechanism" (Ser. No. 08/918, 437); in copending U.S. patent applications of Michael R. Walters entitled "Inertial Tube Indexer" and "Method for Using Inertial Tube Indexer", Ser. No. 09/032,931 and 09/033,367, filed on even date herewith; in copending U.S. patent applications of Michael A. Kelly, Edward G. King, Bradley S. Thomas and Michael R. Walters entitled "Disposable Blood Tube Holder" "Method for Using Disposable Blood Tube Holder", Ser. No. 09/033,373 and 09/033,119, filed on even date herewith; and in copending U.S. patent application of Bradley S. Thomas, Michael A. Kelly, Michael R. Walters, Edward M. Skevington and Paul F. Gaidis entitled "Blood Centrifugation Device with Movable Optical Reader" and "Method of Using Blood Centrifugation Device with Movable Optical Reader", Ser. No. 09/033, 368 and 09/032,934, filed on even date herewith; all of said applications being expressly incorporated herein by reference.

BACKGROUND OF THE INVENTION

The present invention relates generally to a reflector for use with flash tubes. More particularly, the present invention relates to a low-cost reflector that is made of a conductive plastic material and incorporates an integral arc guide for controlling the position of the arc within the flash tube. The reflector is suited for use in an automated hematology system in which a pulse of light from the flash tube causes fluorescence of dyed, density-separated layers of blood cells in a capillary tube during centrifugation, so that a complete blood count can be obtained by optical imaging techniques while the blood sample is being centrifuged.

As part of a routine physical or diagnostic examination of a patient, it is common for a physician to order a complete blood count for the patient. The patient's blood sample may be collected in one of two ways. In the venous method, a syringe is used to collect a sample of the patient's blood in a test tube containing an anticoagulation agent. A portion of the sample is later transferred to a narrow glass capillary tube, known as a sample tube. The open end of the sample tube is placed in the blood sample in the test tube, and a quantity of blood enters the sample tube by capillary action. In the capillary method, the syringe and test tube are not used and the patient's blood is introduced directly into sample tube from a small incision made in the skin. In either case, the sample tube is then placed in a centrifuge, such as the Model 424740 centrifuge manufactured by Becton Dickinson and Company.

In the centrifuge, the sample tube containing the blood sample is rotated at a desired speed (typically 8,000 to 12,000 rpm) for several minutes. The high speed centrifugation separates the components of the blood by density. Specifically, the blood sample is divided into a layer of red blood cells, a buffy coat region consisting of layers of granulocytes, mixed lymphocytes and monocytes, and a plasma layer. The length of each layer can then be optically measured, either manually or automatically, to obtain a count for each blood component in the blood sample. This is possible because the inner diameter of the sample tube and the packing density of each blood component are known, and hence the volume occupied by each layer and the number of cells contained within it can be calculated based on the measured length of the layer. Exemplary measuring devices that can be used for this purpose include those described in U.S. Pat. Nos. 4,156,570 and 4,558,947, both to Stephen C. Wardlaw, and the QBC® "AUTOREAD" hematology system manufactured by Becton Dickinson and Company.

Several techniques have been developed for increasing the accuracy with which the various layer thickness in the centrifuged blood sample can be determined. For example, because the buffy coat region is typically small in comparison to the red blood cell and plasma regions, it is desirable to expand the length of the buffy coat region so that more accurate measurements of the layers in that region can be made. As described in U.S. Pat. Nos. 4,027,660, 4,077,396, 4,082,085 and 4,567,754, all to Stephen C. Wardlaw et al., and in U.S. Pat. No. 4,823,624, to Rodolfo R. Rodriguez et al., this can be achieved by inserting a precision-moldedplastic float into the blood sample in the sample tube prior to centrifugation. The float has approximately the same density as the cells in the buffy coat region, and thus becomes suspended in that region after centrifugation. Since the outer diameter of the float is only slightly less than the inner diameter of the sample tube (typically by about 80 $\mu$m), the length of the buffy coat region will expand to make up for the significant reduction in the effective diameter of the tube that the buffy coat region can occupy due to the presence of the float. By this method, an expansion of the length of the buffy coat region by a factor between 4 and 20 can be obtained. The cell counts calculated for the components of the buffy coat region will take into account the expansion factor attributable to the float.

Another technique that is used to enhance the accuracy of the layer thickness measurements is the introduction of fluorescent dyes (in the form of dried coatings) into the sample tube. When the blood sample is added to the sample tube, these dyes dissolve into the sample and cause the various blood cell layers to fluoresce at different optical wavelengths when they are excited by a suitable light source. As a result, the boundaries between the layers can be discerned more easily when the layer thickness are measured following centrifugation.

Typically, the centrifugation step and the layer thickness measurement step are carried out at different times and in different devices. That is, the centrifugation operation is first carried out to completion in a centrifuge, and the sample tube is then removed from the centrifuge and placed in a separate reading device so that the blood cell layer thicknesses can be measured. More recently, however, a technique has been developed in which the layer thicknesses are calculated using a dynamic or predictive method while centrifugation is taking place. This is advantageous not only in reducing the total amount of time required for a complete blood count to be obtained, but also in allowing the entire procedure to be carried out in a single device. Apparatus and methods for implementing this technique are disclosed in the aforementioned copending applications of Stephen C. Wardlaw entitled "Assembly for Rapid Measurement of Cell Layers" and "Method for Rapid Measurement of Cell Layers".

In order to allow the centrifugation and layer thickness measurement steps to be carried out simultaneously, it is necessary to "freeze" the image of the sample tube as it rotates at high speed on the centrifuge rotor. This can be accomplished by means of a xenon flash lamp assembly that produces an intense excitation pulse of light energy once per revolution of the centrifuge rotor. The pulse of light excites the dyes in the expanded buffy coat area of the sample tube, causing the dyes to fluoresce with light of known wavelengths. The emitted fluorescent light resulting from the excitation flash is focused by a high-resolution lens onto a linear array of charge-coupled devices (CCDs). The CCD array is located behind a bandpass filter which selects the specific wavelength of emitted light to be imaged onto the CCD array.

The xenon flash lamp assembly is one of two sources that are used to illuminate the sample tube while the centrifuge rotor is in motion. The other source is an array of light-emitting diodes (LEDs) which transmit red light through the sample tube for detection by the CCD array through a second bandpass filter. The purpose of the transmitted light is to locate the beginning and end of the plastic float (and hence the location of the expanded buffy coat area), the bottom of the blood column, and the meniscus at the top of the plasma layer. Further details of the optical reading apparatus may be found in the aforementioned copending application of Michael R. Walters entitled "Inertial Tube Indexer", Ser. No. 09/032,931, in the aforementioned copending application of Bradley S. Thomas et al. entitled "Blood Centrifugation Device with Movable Optical Reader", Ser. No. 09/033,368 and in the aforementioned copending application of Michael A. Kelly et al, Ser. No. 09/033,373 entitled "Disposable Blood Tube Holder."

Although xenon flash tube assemblies have been used for many years in photographic cameras and the like, the use of such an assembly in an automated hematology system of the type described above poses certain problems. One problem arises from the need to focus the light from the xenon flash tube onto the expanded buffy coat area of the sample tube in a precise and consistent manner, so that accurate layer thickness measurements can be obtained. To some extent, this can be achieved by mounting the flash tube adjacent to an elliptical reflector having one of its foci coincident with the flash tube axis and the other focus coincident with the axis of the sample tube. Unfortunately, however, the electrical arc that is formed within the bore of the flash tube does not always remain aligned with the longitudinal axis of the tube, but instead tends to wander radially from the tube axis in a random manner. In the past, this problem has been addressed by running an external wire, known as an arc guide, along the outer envelope of the flash tube in a direction parallel to its longitudinal axis. The wire is held at a known potential (usually ground or reference potential) and has the effect of drawing the arc into alignment with the wire and hence with the tube axis. While the use of an external wire as an arc guide is an effective solution, it requires that the flash tube remain in a precise rotational orientation with respect to the reflector in order to focus the light at the desired point. The envelope of the flash tube is rather fragile and can be broken by hard contact with external structures of the type required to maintain such an orientation.

Another technique that has been used is to provide the arc guide in the form of a thin metal strip. The metal strip is mounted independently of the flash tube with its edge held adjacent to the outer glass envelope of the flash tube. This approach avoids the need to maintain the tube in a precise angular orientation, but it results in a rather complex flash tube assembly that is difficult to mass produce.

Accordingly, a need exists for an improved flash tube assembly in which the arc guide function is implemented in a manner that does not require precise rotational alignment of the flash tube and does not create the risk of damage to the outer glass envelope of the tube. A need also exists for a flash tube assembly which incorporates an arc guide feature but is nonetheless simple and inexpensive to manufacture.

SUMMARY OF THE INVENTION

In accordance with one aspect of the present invention, the problems described above are substantially avoided by providing an integral reflector and arc guide for use with a flash tube. The integral reflector and arc guide comprises a reflector structure having a reflective surface that is adapted to be placed in a predetermined orientation with respect to a flash tube having a longitudinal axis. An electrically conductive arc guide is carried by, and is integral with, the reflector structure for controlling the arc in the flash tube. The arc guide comprises an elongated ridge that projects outwardly from the reflecting surface of the reflector structure and extends along the reflecting surface in a direction substantially parallel to the longitudinal axis of the flash tube. An electrical terminal is also carried by the reflector structure and has an electrical connection to the arc guide for allowing an electrical potential to be applied to the arc guide. In a preferred embodiment, the elongated ridge has a substantially triangular cross-section, with an apex of the triangle projecting outwardly from the reflecting surface and forming a knife edge that is adapted to be positioned close to, or in contact with, the outer envelope of the flash tube.

In another aspect, the present invention relates to a combined reflector and arc guide for use with a flash tube. The combined reflector and arc guide comprises a reflector structure having a reflective surface that is adapted to be placed in a predetermined orientation with respect to a flash tube. The reflector structure is made of an electrically conductive plastic material. An electrically conductive arc guide is carried by the reflector structure for controlling the arc in the flash tube, and extends along the reflective surface of the reflector structure in a direction substantially parallel to the longitudinal axis of the flash tube. An electrical terminal is also carried by the reflector structure and has an electrical connection to the arc guide by conduction directly through the plastic material of the reflector structure, so that an electrical potential can be applied to the arc guide.

In accordance with a further aspect of the present invention, a reflector for use with a flash tube comprises a reflector structure having a reflective surface that is adapted to be placed in a predetermined orientation with respect to a flash tube. The reflecting surface has an area of modified reflectivity, preferably in the form of a series of grooves, that is located so as to correspond to the area of peak intensity of the flash tube. The grooves serve to spread out the peak intensity in the center of the flash tube, so that light produced by the flash tube is focused uniformly across the area to be illuminated.

BRIEF DESCRIPTION OF THE DRAWINGS

The various objects, advantages and novel features of the present invention will be more readily appreciated from the following detailed description when read in conjunction with the appended drawings, in which:

FIG. 5 is a front elevational view of the flash tube reflector used in the flash tube assembly of FIGS. 2–4;

FIG. 6 is a side cross-sectional view of the flash tube reflector of FIG. 5, taken along the line 6–6 in FIG. 5;

FIG. 7 is a detailed view of a portion of the front surface of the flash tube reflector shown in FIG. 5; and FIG. 8 is a side view of the flash tube reflector similar to that of FIG. 6, illustrating the locations of the foci of the elliptical reflector surface.

Throughout the drawings, like reference numerals will be understood to refer to like parts and components.

DETAILED DESCRIPTION OF THE PREFERRED EMBODIMENT

Figure 1:
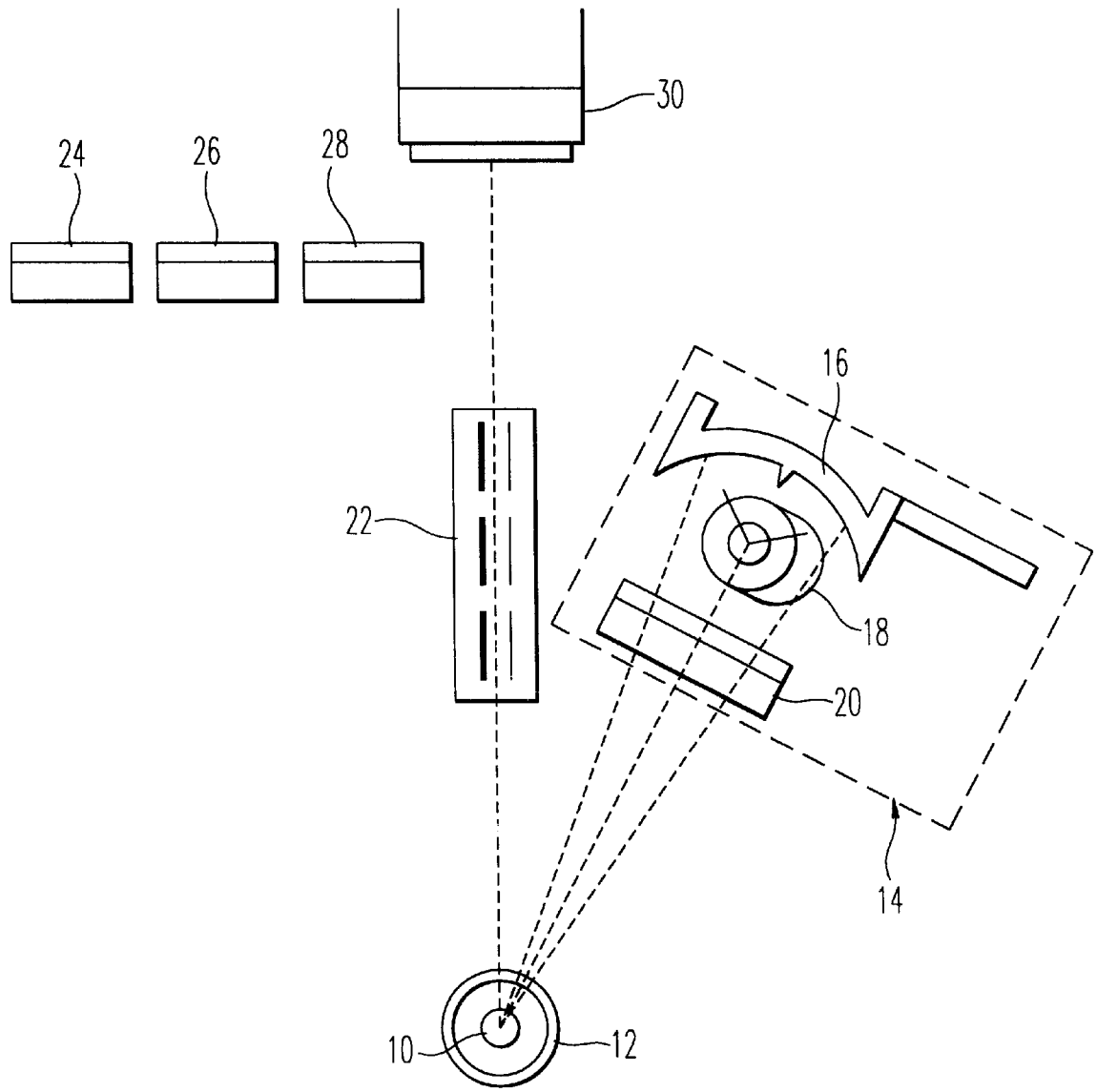
FIG. 1 is a schematic illustration of an automated hematology system in which the flash tube reflector of the present invention may be employed.

FIG. 1 is a schematic illustration of a portion of an automated hematology system in which the flash tube reflector of the present invention may be employed. A sample tube 10 (shown in cross-section) containing a blood sample to be analyzed is held in a protective, transparent carrier tube 12. The carrier tube 12 is, in turn, mounted in the rotor of a high-speed centrifuge (not shown) which separates the components of the blood sample according to their respective densities. A flash tube assembly 14 is mounted above the centrifuge rotor which carries the sample tube 10 and the carrier tube 12. The flash tube assembly 14 includes a reflector 16, a xenon flash tube 18 and a blue excitation filter 20. Illumination from the flash tube 18 is focused by the reflector 16 and passes through the excitation filter 20 to impinge on the sample tube 10 within the carrier tube 12. A second illumination source (not shown) consists of an array of LEDs mounted below the rotor and carrier tube 12.

With continued reference to FIG. 1, excitation of the dyed and compacted blood cell layers in the sample tube 10 by the flash tube 18 and filter 20 causes the blood cell layers to fluoresce at selected optical wavelengths. The light produced by the fluorescing blood cell layers is focused by a high-resolution SELFOC lens array 22 and passes through one of three different optical filters 24, 26 and 28 which are selectively moved into the path of the light by means of an automatic actuating system (not shown). The optical filter 24 is a blue blocking filter, while the optical filters 26 and 28 are red and green emission filters, respectively. The filters 24 and 28 are used in conjunction with the flash lamp assembly 14 for detecting the lengths of the various layers of the buffy coat region of the centrifuged blood sample, while the red emission filter 26 is used in connection with the LED array (not shown) to determine the float and meniscus locations in the sample tube 10. The light which passes through the optical filters 24, 26 and 28 is detected by a linear CCD array 30, which consists of 2,080 individual photodetectors spaced on 10-micron centers to provide a resolution of 0.0005 inch or better.

In practice, all of the components shown in FIG. 1 (except for the sample tube 10 and the carrier tube 12) are mounted on a movable carriage which is mounted above the centrifuge rotor. The direction of carriage movement is perpendicular to the plane of the drawing in FIG. 1, and is parallel to the axes of the sample tube 10 and carrier tube 12 when these tubes are moved to the orientation shown in FIG. 1 by the centrifuge rotor. Since the length of the CCD array is approximately one-third the length of the sample tube 10, the movable carriage allows the CCD array to capture an image of the entire length of the sample tube 10 by moving or indexing the carriage three times during a given measurement cycle. The expanded buffy coat area of the sample tube 10 can be imaged by the CCD array while the carriage is in its middle position, with the other two carriage positions being used (in conjunction with the LEDs described previously) to locate the float and meniscus positions in the sample tube 10. Further details concerning the construction and operation of the movable carriage can be found in the aforementioned copending application of Bradley S. Thomas et al. entitled "Blood Centrifugation Device with Movable Optical Reader", Ser. No. 09/033,368.

In order to compensate for irregular or uneven boundaries between the blood cell layers in the sample tube 10, readings are made eight times at equally spaced locations around the circumference of the sample tube 10 by rotating or indexing the carrier tube 12 in which the sample tube 10 is held. This is accomplished by means of an inertial indexing mechanism which utilizes momentary and intentional variations in the speed of the centrifuge rotor to rotate the carrier tube 12 through defined angular increments. Further details of the indexing mechanism can be found in the aforementioned copending application of Michael R. Walters entitled "Inertial Tube Indexer", Ser. No. 09/032,931.

Figure 2:
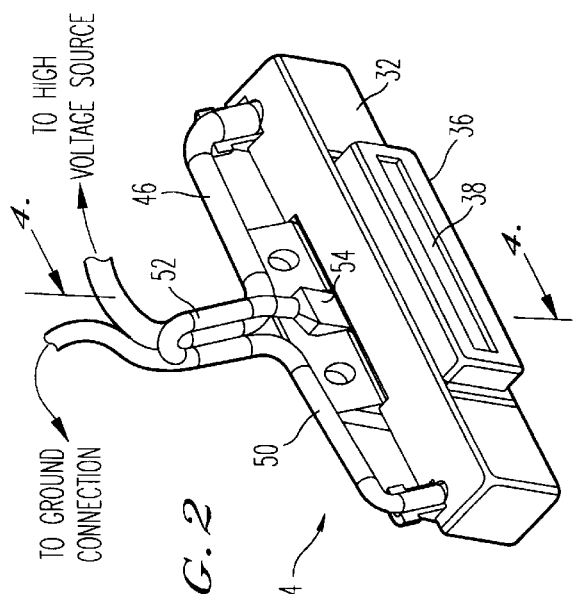
FIG. 2 is a perspective view of an assembled flash tube assembly incorporating a flash tube reflector in accordance with a preferred embodiment of the present invention.
Figure 3:
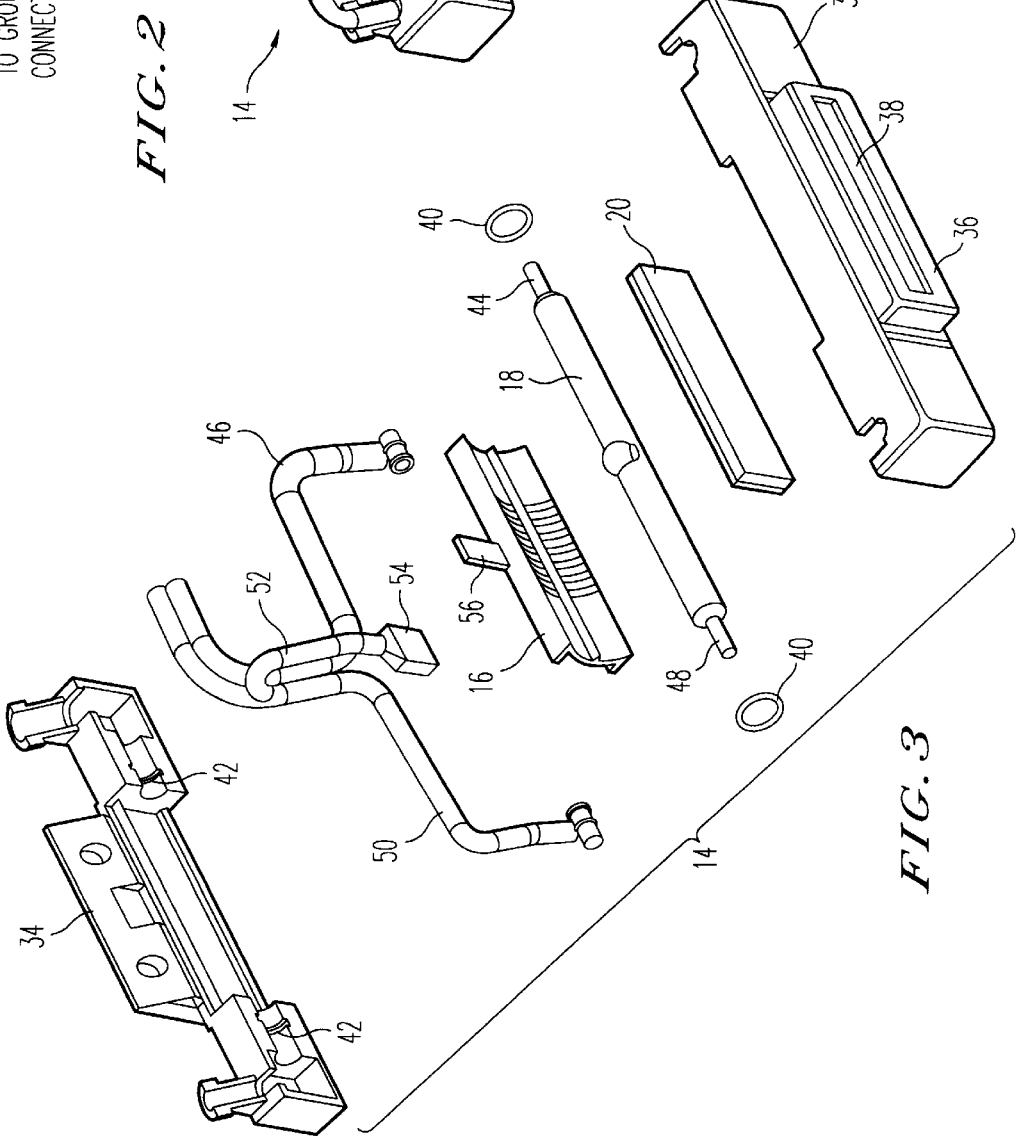
FIG. 3 is an exploded view of the flash tube assembly shown in FIG. 2, with the flash tube reflector shown in perspective.
Figure 4:
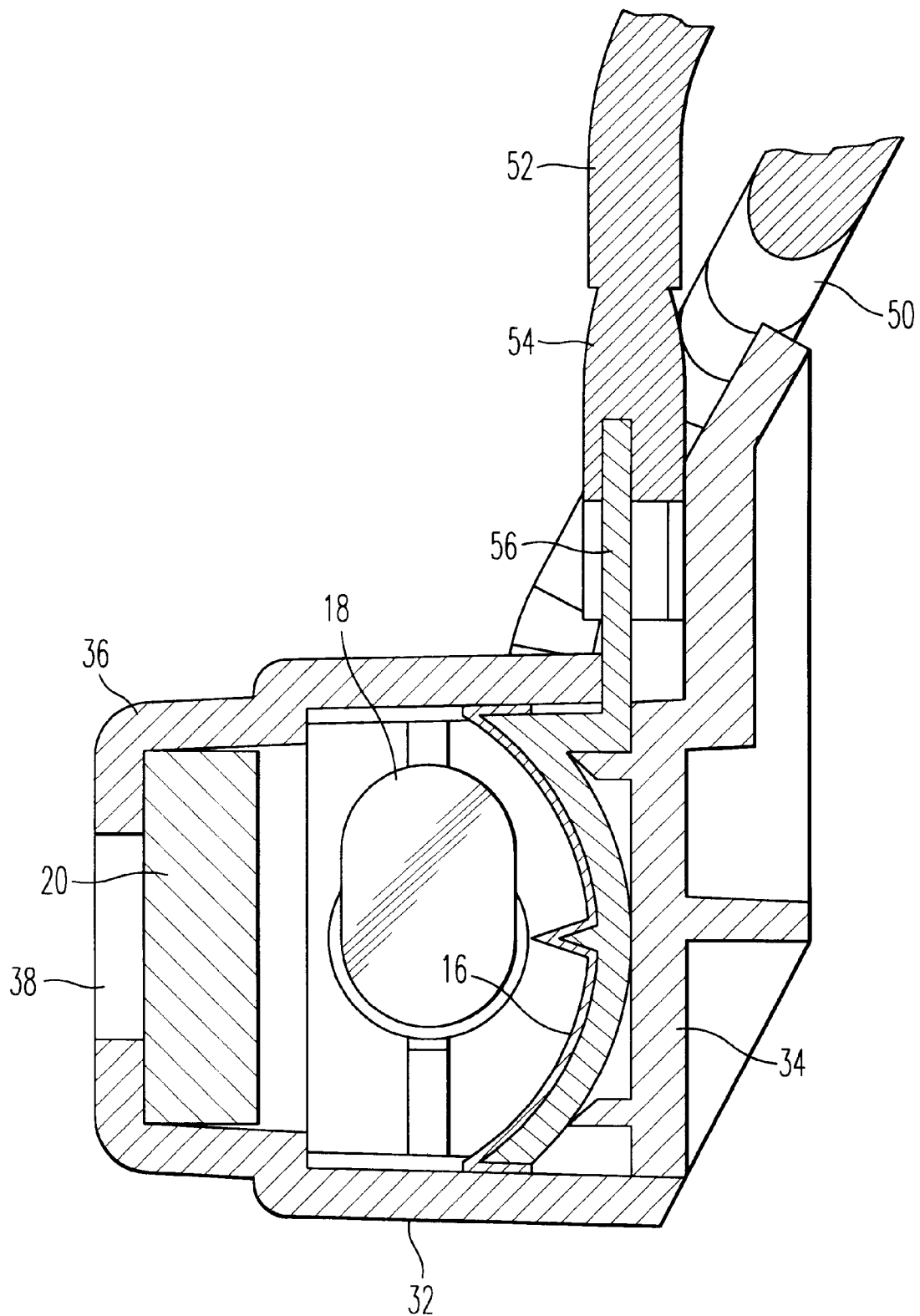
FIG. 4 is a sectional view of the flash tube assembly taken along the line 4—4 in FIG. 2.

FIGS. 2–4 illustrate the details of the xenon flash tube assembly 14 shown in FIG. 1. The assembly 14 includes an enclosure consisting of a front cover portion 32 and a rear mounting portion 34, the latter serving to mount the assembly 14 on the movable carriage referred to previously. The internal components of the flash tube assembly 14, which are captured between the cover portion 32 and rear mounting portion 34, include the reflector 16, the xenon flash tube 18 and the blue excitation filter 20. The blue excitation filter 20, which transmits light at a wavelength of approximately 470 nanometers, is housed in a protruding forward portion 36 of the front cover 32. A narrow rectangular slot or window 38 is provided in this portion to allow light to be emitted from the flash tube assembly 14. The xenon flash tube 18 is mounted behind the filter 20 and is supported by two silicone rubber O-rings 40 which are received in corresponding grooves 42 (visible in FIG. 3) formed in the rear mounting portion 34 of the enclosure. Similar grooves (not visible in FIG. 3) are formed in the front cover portion 32 of the enclosure. The xenon flash tube 18 is a commercially-available unit having a 3 millimeter bore and a 1.4-inch arc length. A suitable flash tube is the Model FXQSL-35-1.4 xenon flash tube manufactured by EG&G Optoelectronics of Salem, Mass. The electrode 44 at one end of the flash tube 18 is connected to a high-voltage line 46, and the electrode 48 at the opposite end of the flash tube 18 is connected to a ground or reference line 50. A tap 52 from the ground or reference line 50 terminates in a connector 54 which is coupled to an integral tab 56 formed on the reflector 16 for a purpose to be described shortly. Since the xenon flash tube 18 operates at a voltage of between 500 and 1,000 volts DC, the lines 46, 50 and 52 are provided with suitable high-voltage insulation as shown.

Power to the xenon flash lamp 18 is provided by a programmable high-voltage power supply that is capable of operating at the desired 500 to 1,000 volt DC level with a maximum wattage of 10 watts. The power supply is capable of recharging its storage capacitors to 1,000 volts DC in less than 250 milliseconds. Operation over this voltage range provides a 15-microsecond pulse of light with between 0.25 and 2.5 joules of energy at a maximum repetition rate of three flashes per second. This mode of operation represents a derating of approximately 10 percent, allowing the lamp to provide an estimated 10 million flashes during its lifetime. A suitable high-voltage power supply is the Model LS-226 unit manufactured by EG&G Optoelectronics of Salem, Mass. The high-voltage power supply, which has been omitted from FIGS. 2–4 for clarity, has its output lines coupled to the lines 46 and 50 shown in the drawings.

FIGS. 5–7 illustrate the details of the flash tube reflector 16 that is the principal subject of the present invention. The reflector 16 comprises a reflector structure or body 58 that is made of a conductive plastic or resin material. An example of such a material is carbon-filled Noryl, available from General Electric Company of Pittsfield, Mass. This material has a volume resistivity of approximately 8,000 ohm-cm, and allows for direct electrical conduction through the body of the reflector structure 58 for a purpose to be described shortly. The reflector structure 58 has a rectangular shape when viewed from the front, as shown in FIG. 5. When viewed from the side, as shown in FIG. 6, the reflector structure 58 has the shape of a partial ellipse with one focus 60 approximately coincident with the inside wall of the xenon flash tube 18 nearest to the reflector. On the side of the reflector structure 58 which faces the flash tube 18, a highly reflective metallic layer 62 is provided to serve as a reflecting surface for the light produced by the flash tube 18. In the preferred embodiment, the layer 62 is a vacuum-deposited aluminum mirror coating having a thickness of approximately 5 to 10 microns (the thickness of this layer has been exaggerated in FIG. 6 for illustration purposes). A transparent protective coating made of lacquer or the like (not shown in FIG. 6) may be applied over the reflective layer 62 to prevent oxidation. Alternatively, the metallic layer 62 may be made of a material that does not oxidize (e.g., a vacuum-depositedgold mirror coating).

In accordance with an important feature of the present invention, the reflector structure 58 is formed with an integral ridge 64 which projects outwardly from the reflecting surface 62 and extends longitudinally along the reflecting surface 62 in a direction parallel to the longitudinal axis of the flash tube 18. As best seen in FIG. 6, the ridge 64 has a triangular cross-section with the apex or vertex of the triangle projecting outwardly from the reflecting surface 62 and forming a knife edge 66. In the preferred embodiment, the knife edge 66 is formed by providing the apex of the triangle with a radius of about 0.003 inch. When the flash tube assembly of FIGS. 2–4 is fully assembled, the knife edge 66 is spaced away from the outer sapphire envelope of the flash tube 18 by a uniform distance of about 0.010 inch. If desired, however, the knife edge can be positioned in direct contact with the outer envelope of the flash tube 18, provided that the contact force is kept small enough that breakage of the outer envelope of the flash lamp 18 does not occur.

During operation of the flash lamp assembly 14 of FIGS. 2–4, the ridge 64 serves as an arc guide for controlling the position of the arc within the xenon flash tube 18. Due to the electrical conductivity of the plastic material of which the reflector structure 58 is made, a conductive path exists between the tab 56 and the arc guide 64 directly through the body of the reflector structure 58. For a reflector structure made of carbon-filled Noryl and having the dimensions specified below, an electrical resistance of only about 6 ohms exists between the tab 56 and the arc guide 64. It will be appreciated that the electrical conductivity of the reflector structure 58 is advantageous in that it avoids the need to provide a separate electrical conductor between the tab 56 and the arc guide 64. Moreover, by forming the tab 56, reflector structure 58 and arc guide 64 as a single molded part, the cost of the flash tube assembly 14 is reduced and difficulties in manufacturing and assembly are minimized. It will also be apparent that, since the arc guide 64 is fixed relative to the reflector structure 58, it is not necessary to maintain the flash tube 18 in a fixed rotational orientation in order to locate the arc at the focal point of the reflector 16.

In accordance with another feature of the present invention, the reflector 16 is fabricated in such a way as to compensate for variations in light output along the length of the flash tube 18. It is a characteristic of xenon flash tubes that the light intensity at the center of the tube tends to be somewhat greater than the light intensity at either end of the tube. For the purposes of the present invention, this is disadvantageous since the object is to illuminate the desired section of the sample tube 10 (i.e., the buffy coat region) in a uniform manner. To achieve this object, the reflective surface of the reflector structure 58 is formed with an area of modified reflectivity in the form of a plurality of shallow grooves 68 (seven in the preferred embodiment) which are oriented in a direction normal to the arc guide 64 and the longitudinal axis of the flash lamp 18. The grooves 68 are formed only in the central portion of the reflective surface 62 of the reflector structure 58, and span a distance which approximately corresponds to the peak intensity region of the flash tube 18. The grooves 68 have triangular cross-sections, as shown in FIG. 7, and serve to disperse or diffuse some of the light produced at the center of the flash tube toward the outer ends of the reflector structure 58. As a result, the peak intensity at the center of the flash tube 18 is spread out somewhat, and the light output from the reflector 16 is more uniform. It will be appreciated that the number, spacing, depth and orientation of the grooves 68 need not be as shown in the drawings, and may be varied to suit the requirements of specific flash tubes and reflector configurations.

Other methods may be used in place of the grooves 68 to spread out the peak intensity of the xenon flash tube 18. For example, the grooves 68 may be replaced by an area of the reflective surface that is faceted, textured or roughened in order to redirect and/or reduce the light produced at the center of the flash tube 18. The use of grooves is preferred, however, since it is less sensitive to the process used to form reflective surface than texturing or roughening, for example.

In a preferred embodiment of the present invention, the reflector structure 58 of FIGS. 5–7 is approximately 1.5 inches in length (measured in the horizontal direction in FIG. 5) and approximately 0.5 inch in height (excluding the tab 56). The depth of the reflector structure 58 (i.e., the horizontal dimension of the reflector structure in FIG. 6) is about 0.175 inch. The wall thickness of the reflector structure 58 behind the reflective surface 62 is approximately 0.050 inch. The triangular ridge 64 which forms the arc guide subtends an angle of about 30°, and the knife edge 66 projects above the reflective surface 62 by about 0.055 inch. The tab 56 has a length of 0.25 to 0.3 inch, a width of about 0.18 inch, and a thickness of about 0.035 inch. Each of the grooves 68 has a width of about 0.035 inch, a maximum depth of about 0.013 inch, and subtends an angle of about 106°. The grooves 68 are spaced uniformly on 0.1 inch centers, with the outermost grooves being spaced inwardly from the ends of the reflector structure 58 by about 0.45 inch. It will be appreciated that these dimensions are merely exemplary and may be varied to suit the requirements of particular applications.

FIG. 8 is a diagrammatic view which illustrates the elliptical geometry of the reflective surface 62 of the reflector structure 58. The reflective surface 62 forms a portion of an imaginary ellipse 70 having a major axis of about 1.4 inches and a minor axis of about 0.8 inch. The distance between the foci 60 and 72 of the ellipse 70 is about 1.15 inch. In use, the reflector structure 58 is positioned such that the focus 60 is approximately coincident with the inner wall of the flash tube 18 (to which the arc is drawn by the arc guide 64) and the focus 72 is approximately coincident with the longitudinal axis of the sample tube 10. The knife edge 66 of the arc guide is preferably spaced away from the outer sapphire envelope of the flash tube 18 by a uniform distance of between 0.005 inch and 0.025 inch, with the preferred separation being about 0.010 inch. As indicated previously, the knife edge 66 may be placed in direct contact with the outer envelope of the flash tube 18 if desired, but care must be taken to insure that the contact force is low enough to prevent the risk of tube breakage. Again, it should be emphasized that all of the foregoing dimensions are merely exemplary and are not intended to limit the scope of the present invention.

One of the advantages of the novel reflector disclosed herein is that it allows the flash tube to be operated at a derated voltage, thereby extending the life of the flash tube. Typically, a consequence of using a reduced flash tube voltage is that the arc (which usually fills the flash tube in a high-energy discharge) wanders randomly around the bore of flash tube, making it difficult to focus the light produced by the tube. With the present reflector, the location of the arc is controlled by the arc guide during low-energy discharges, making it possible to operate the flash tube at reduced voltages while preserving the ability to accurately focus the light produced by the flash tube.

Although the foregoing description represents the preferred embodiment of the invention, several modifications are possible. For example, although it is preferable to form the reflector structure 58 and arc guide 64 as a single piece, it is possible to form the arc guide 64 as a separate element which is carried by the reflector structure 58 or by an adjacent structure. It is also possible to provide a separate electrical conductor for applying a potential to the arc guide 64, and in that event the plastic material of the reflector structure 58 need not be electrically conductive. As a further alternative, the reflector structure 58 and/or the arc guide 64 can be made of an electrically conductive material other than conductive plastic, such as metal. As a still further alternative, the desired electrical conductivity may be provided by the metallized layer 62 on the surface of the reflector structure 58, rather than by the body of the reflector structure 58, although in this case a somewhat thicker metallized layer may be needed in order to insure that an adequate level of conductivity will exist.

Those skilled in the art will readily appreciate that many other modifications are possible in the exemplary embodiments without materially departing from the novel teachings and advantages of this invention. Accordingly, all such modifications are intended to be included within the scope of the invention as defined in the following claims.

What is claimed is:

1. An integral reflector and arc guide for use with a flash tube, comprising:

a reflector structure having a reflecting surface adapted to be placed in a predetermined orientation with respect to a flash tube having a longitudinal axis;

an electrically conductive arc guide carried by and integral with said reflector structure for controlling an arc in said flash tube, said arc guide comprising an elongated ridge projecting outwardly from said reflecting surface and extending along said reflecting surface in a direction substantially parallel to the longitudinal axis of said flash tube; and an electrical terminal carried by said reflector structure and having an electrical connection to said arc guide for allowing an electrical potential to be applied to said arc guide.

2. An integral reflector and arc guide as claimed in claim 1, wherein said elongated ridge has a substantially triangular cross-section with an apex of said triangle projecting outwardly from said reflecting surface and forming a knife edge adapted to be positioned close to or in contact with an outer envelope of said flash tube.

3. An integral reflector and an arc guide as claimed in claim 1, wherein said reflecting surface has an elliptical curvature in a direction substantially perpendicular to the direction in which said ridge extends.

4. An integral reflector and arc guide as claimed in claim 1, wherein said reflector structure is made of an electrically conductive plastic material, said electrically conductive plastic material providing said electrical connection between said electrical terminal and said arc guide.

5. An integral reflector and arc guide as claimed in claim 4, wherein said electrical terminal comprises a tab made of said conductive plastic material and formed integrally with said reflector structure.

6. An integral reflector and arc guide as claimed in claim 4, wherein said reflecting surface comprises a reflective layer carried by said reflective structure.

7. An integral reflector and arc guide as claimed in claim 6, wherein said reflective layer comprises a vacuum-deposited metallic coating.

8. An integral reflector and arc guide as claimed in claim 7, further comprising a transparent protective layer overlying said metallic coating for preventing oxidation of said metallic coating.

9. An integral reflector and arc guide as claimed in claim 1, wherein said reflecting surface has an area of modified reflectivity to disperse or diffuse light produced by the flash tube, said area occupying only a portion of said reflecting surface which corresponds approximately to the intensity peak of said flash tube.

10. An integral reflector and arc guide as claimed in claim 9, wherein said area of modified reflectivity is provided in the form of a plurality of grooves in said reflecting surface, said grooves being substantially parallel to each other and extending in a direction substantially perpendicular to the direction in which said ridge extends.

11. A reflector as claimed in claim 1, wherein said flash tube has a longitudinal axis, and wherein said area of modified reflectivity is provided in the form of a plurality of grooves in said reflecting surface, said grooves being substantially parallel to each other and extending in a direction substantially perpendicular to the longitudinal axis of said flash tube.

12. A combined reflector and arc guide for use with a flash tube, comprising:

a reflector structure having a reflective surface adapted to be placed in a predetermined orientation with respect to a flash tube, said reflective structure being made of an electrically conductive plastic material;

an electrically conductive arc guide carried by said reflector structure for controlling an arc in said flash tube, said arc guide extending along said reflecting surface in a direction substantially parallel to the longitudinal axis of said flash tube; and an electrical terminal carried by said reflector structure and having an electrical connection to said arc guide by conduction directly through said conductive plastic material for allowing an electrical potential to be applied to said arc guide.

13. A combined reflector and arc guide as claimed in claim 12, wherein said arc guide comprises an elongated ridge projecting outwardly from said reflecting surface.

14. A combined reflector and arc guide as claimed in claim 13, wherein said elongated ridge has a substantially triangular cross-section with an apex of said triangle projecting outwardly from said reflecting surface and forming a knife edge adapted to be positioned close to or in contact with an outer envelope of said flash tube.

15. A combined reflector and arc guide as claimed in claim 12, wherein said reflecting surface has an elliptical curvature in a direction substantially perpendicular to the direction in which said ridge extends.

16. A combined reflector and arc guide as claimed in claim 12, wherein said electrical terminal comprises a tab made of said conductive plastic material and formed integrally with said reflector structure.

17. A combined reflector and arc guide as claimed in claim 12, wherein said reflecting surface comprises a reflective layer carried by said reflective structure.

18. A combined reflector and arc guide as claimed in claim 17, wherein said reflective layer comprises a vacuum-deposited metallic coating.

19. A combined reflector and arc guide as claimed in claim 18, further comprising a transparent protective layer overlying said metallic coating for preventing oxidation of said metallic coating.

20. A combined reflector and arc guide as claimed in claim 12, wherein said reflecting surface has an area of modified reflectivity to disperse or diffuse light produced by the flash tube, said area occupying only a portion of said reflecting surface which corresponds to approximately the intensity peak of said flash tube.

21. A combined reflector and arc guide as claimed in claim 20, wherein said area of modified reflectivity is provided in the form of a plurality of grooves in said reflecting surface, said grooves being substantially parallel to each other and extending in a direction substantially perpendicular to the direction in which said ridge extends.

22. A reflector for use with a flash tube, comprising a reflector structure having a reflecting surface adapted to be placed in a predetermined orientation with respect to a flash tube, said reflecting surface having an area of modified reflectivity to disperse or diffuse light produced by the flash tube, said area occupying only a portion of said reflecting surface which corresponds to approximately the intensity peak of said flash tube.

* * * * *